(12) United States Patent
Prager

(10) Patent No.: US 6,641,551 B1
(45) Date of Patent: Nov. 4, 2003

(54) COTTON BUDS AND SWABS FOR MEDICAL USE

(76) Inventor: Robert Prager, Luitgardisstr. 4a, D-46446 Emmerich (DE)

( * ) Notice: Subject to any disclaimer, the term of this patent is extended or adjusted under 35 U.S.C. 154(b) by 0 days.

(21) Appl. No.: 09/856,918

(22) PCT Filed: Apr. 19, 2000

(86) PCT No.: PCT/EP00/03529

§ 371 (c)(1), (2), (4) Date: May 30, 2001

(87) PCT Pub. No.: WO00/64397

PCT Pub. Date: Nov. 2, 2000

(30) Foreign Application Priority Data

Apr. 22, 1999 (DE) .......................... 199 18 426

(51) Int. Cl.$^7$ .............................................. A61M 35/00
(52) U.S. Cl. ........................ 604/1; 15/143.1; 15/159.1
(58) Field of Search ........................... 604/1–3; 15/106, 15/143.1, 159.1, 160

(56) References Cited

U.S. PATENT DOCUMENTS 2,510,490 A * 6/1950 Ager
3,618,609 A * 11/1971 Glick et al.
4,568,326 A * 2/1986 Rangaswamy
4,776,836 A * 10/1988 Stanley
4,951,684 A * 8/1990 McMillan
5,152,742 A * 10/1992 Simpson

FOREIGN PATENT DOCUMENTS

| DE | 1741279 | 3/1957 |
| DE | 1183641 | 12/1964 |
| DE | 1188775 | 3/1965 |
| DE | 3709497 | 11/1987 |
| DE | 19642431 | 4/1998 |
| EP | 0 363 533 | * 4/1990 |
| FR | 2129143 | 10/1972 |

* cited by examiner

*Primary Examiner*—Dennis Ruhl
(74) *Attorney, Agent, or Firm*—Venable LLP; Norman N. Kunitz

(57) ABSTRACT

The invention relates to cotton buds and to swabs for medical use. The inventive buds or swabs are characterized in that they are extruded and provided with a continuous inner web. Said inner web may be linked with the inner surface of the buds or swabs by webs that are produced of the same material. The invention provides buds or swabs that are slightly less rigid while guaranteeing good working properties and a good usability. At the same time, their weight and the material required is considerably reduced.

4 Claims, 2 Drawing Sheets

COTTON BUDS AND SWABS FOR MEDICAL USE

BACKGROUND OF THE INVENTION

Plastic rods for cotton ear swabs and swabs for medical use are primarily extruded continuously and are then cut to specific lengths. They are rarely produced as injection-molded parts. Injection-molded rods are solid (FIGS. 1a and 1b) and consequently weigh a lot.

German Patent 196 42 431 A 1 describes an inter-dental cleaner for a similar use, comprising a rod-shaped, elongated carrier of a first material, which is covered in some surface areas by at least one insert or overlay of a second material that is softer than the first material. The carrier cross section described therein is essentially an optional, in particular oval, round, triangular or flattened shape. The cross section for the selected insert or overlay is also essentially optional, wherein especially oval, round, flattened or triangular shapes are used. However, this method requires the use of several materials. Also, the weight is relatively high because of the high material use.

German Patent 37 09 497 A 1 relates to a mouth swab rod stabilized with a support rod. Owing to the high material use, a swab rod of this type becomes relatively heavy and expensive to produce. Furthermore, a loosely inserted support rod results in an increased danger of injury in case of a rod break.

German Patent 17 41 279 U describes a rod for cotton swabs. The rod is produced from twisted-together cotton and is coated with an adhesive-type coating for the purpose of increasing the rigidity. The rod rigidity is further increased through an inserted layer of Perlon® wire or other suitable plastic. To be sure, this method leads to an increase in the rigidity, but results in the disadvantage of a high material use and thus leads to a weight increase.

Continuously extruded rods are hollow (FIGS. 2a and 2) and are therefore relatively lightweight.

Continuously extruded cotton ear swab rods, which the invention relates to, have standard lengths of 70 to 73 mm and an outside diameter of 1.5 to 2.8 mm. The inside diameter changes with increasing or decreasing rod weight.

Cotton ear swab rods and the rods of swabs for medical use primarily differ as to the rod dimensions and the fact that swabs for medical use usually have cotton wound around only one end of the rod (FIG. 3). Standard dimensions for the swab rods for medical use are approximately 1.5 mm to 6.0 mm, wherein the rod length ranges from approximately 100 mm to 400 mm. One exemplary embodiment for a standard swab rod for medical use is 140 mm long and has an outside diameter of 4.0 mm.

For a non-problematic further processing, both types of rods require a certain amount of flexural strength, so that they do not bend overly much and jump out of the guide for the winding machine.

The standard rod weights used nowadays are necessary to achieve sufficient rigidity for a further processing and to have sufficient material for the "sealing-in."

Sealing-in means that the rod ends have jagged, melted-on areas on the ends, so that subsequently the cotton can stick to the still soft plastic and can then be wound into a specific shape (FIG. 3).

Owing to a notching effect or "a sealing together", this sealing-in operation can weaken the hollow rod to a degree that it can break off during the winding of the cotton head already or later on during the use, maybe even in the ear. (See FIG. 4)

In particular, these dangers exist with thin-walled cotton ear swab rods. In the past, experiments were conducted to reduce the rod weight by reducing the wall thickness and to prevent the "sealing through" with the aid of grooves on the inside and the outside of the rod (FIGS. 5a and 5b respectively). However, these profiles did not lead to an increase in the flexural strength. A further reduction in the rod weight to below the weights presently standard in the marketplace, given the same workability for cotton ear swabs, was therefore made impossible.

Similar problems as for the cotton ear swabs were encountered for the further processing of swabs for medical use. However, the danger of a sealing through (FIG. 4) is not as high as for the cotton ear swab rods because of the higher wall thickness that is standard for the rods of swabs for medical use.

SUMMARY OF THE INVENTION

The above problems generally are achieved according to the present invention by a cotton ear swab device or a swab device used for medical purposes, comprising a rod having a swab on at least one end thereof, with the rod being a continuously hollow extrusion including an outer shell provided with a continuous internal web. Preferably, the internal web is connected once or several times to an internal surface of the shell, either continuously or in sections, with the webs being made of the same material as the shell. Still more preferably, the internal web is connected to the internal surface of the shell at least at three points distributed about the circumference of the internal surface.

DESCRIPTION OF THE PREFERRED EMBODIMENT

Figure 1A:
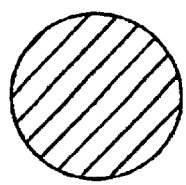
FIGS. 1a and 1b are a cross-sectional view and a longitudinal sectional view, respectively, of a known solid rod for a cotton swab.
Figure 1B:
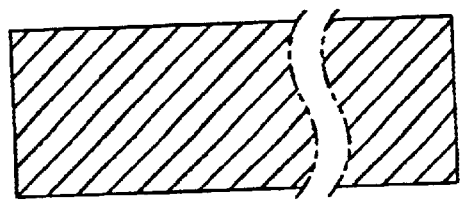
Figure 2A:
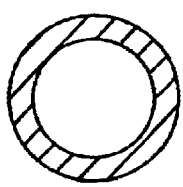
FIGS. 2a and 2b are a cross-sectional view and a longitudinal-sectional view, respectively, of a known hollow rod, for example, an extrusion, for a cotton swab.
Figure 2B:
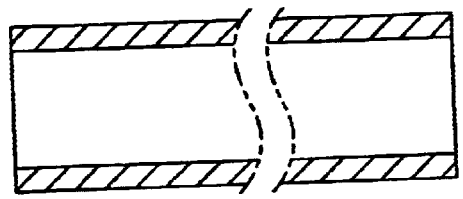
Figure 3:
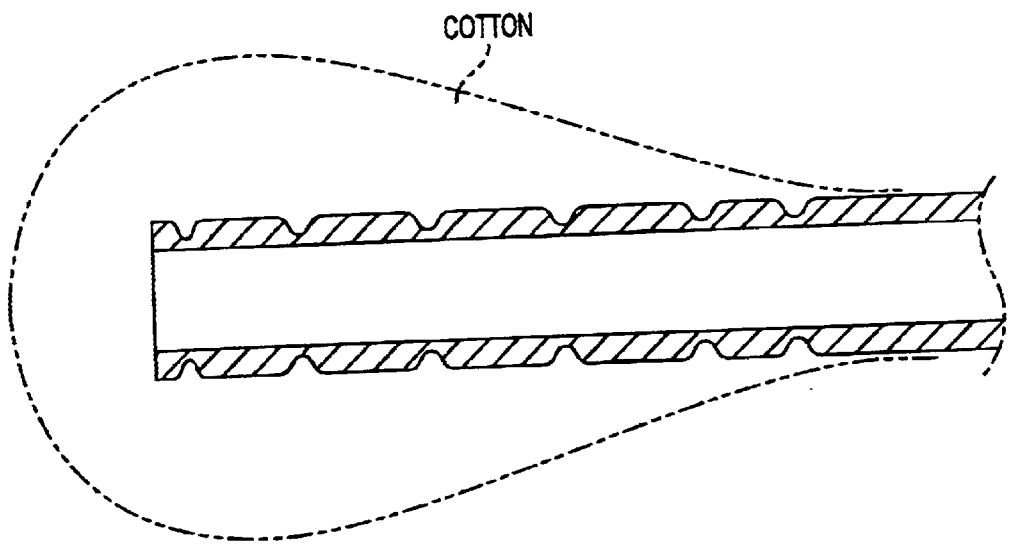
FIG. 3 is a partial longitudinal sectional view of a known hollow rod, i.e., an extrusion, for a cotton swab, with the cotton swab shown in phantom and with the exterior of the rod provided with notches or ridges at one end.
Figure 4:
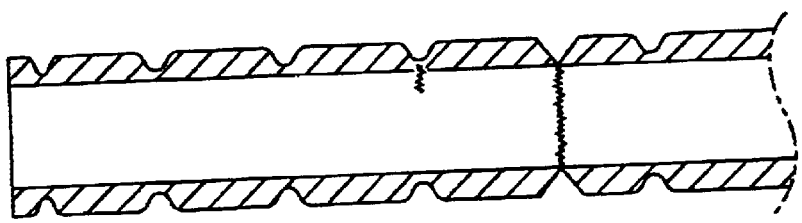
FIG. 4 is a partial longitudinal sectional view of the known hollow rod of FIG. 3 indicating a failure or rupture at one of the notches.
Figure 5A:
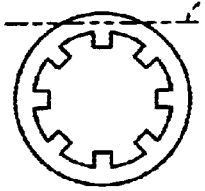
FIGS. 5a and 5b are cross-sectional views of a known hollow rod, i.e., an extrusion, for a cotton swab, provided with inwardly directed and outwardly directed groves, respectively.
Figure 5B:
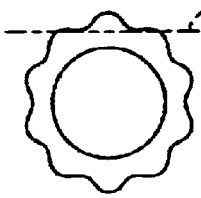
Figure 6A:
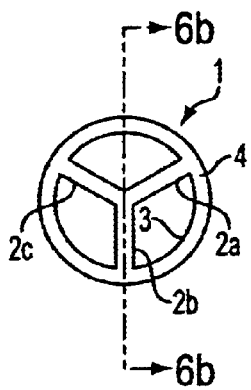
FIGS. 6a, 6b and 6c are cross-sectional, longitudinal sectional and perspective views respectively, of an extrusion constituting a rod for a cotton swab.
Figure 6B:
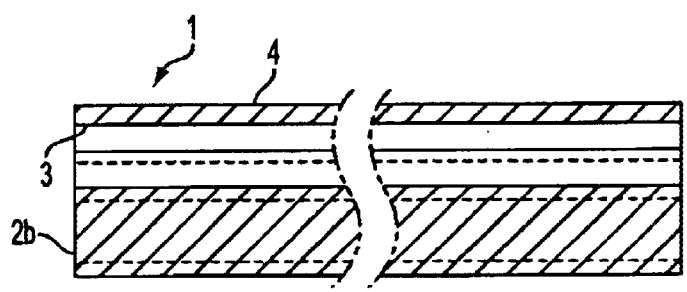
Figure 6C:
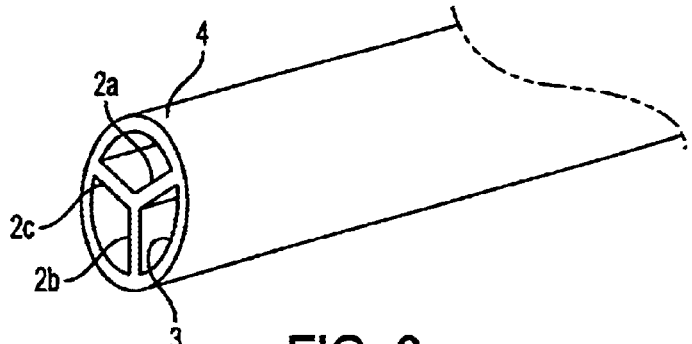

The rod with internal webs shown in FIGS. 6a–6c solves the problem of the decreasing flexural strength at reduced weight, as well as the problem of the head breaking off as a result of the sealing in.

Figure 7A:
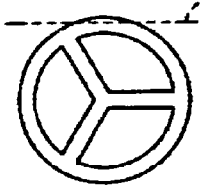
FIGS. 7a, 7b and 7c are cross-sectional views of the rod according to FIGS. 6a–6c in different rotational positions.
Figure 7B:
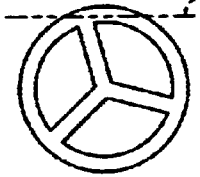
Figure 7C:
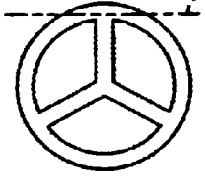

Owing to the closed inside profile, the sealed-in rod 1 with the lower wall thickness does no longer break off, even if the outside wall is sealed through because at least one internal web 2a–2c always remains undamaged and the two other webs can be sealed only to some degree. (FIGS. 7a–7c)

The triangular composite design of the internal webs 2a–2c, wherein the webs each extend from a common point in a radial direction and are fixedly and continuously connected to the internal surface 3 of the outer shell 4 of the hollow rod extrusion 1, results in a high rigidity with clearly reduced wall thickness. To be sure, the rigidity decreases slightly, but this deficit is compensated during the movement of winding the cotton around in that the stabilized webs continuously prevent a breaking off. In this way, weight savings of 15 to 55% are realized as compared to the present standard weights.

By reducing the weight, it is possible above all to save material, which preserves resources and results in purchasing advantages for the consumer. Other side effects are lower carton and pallet weights.

What is claimed is:

1. A cotton ear swab or a swab device used for medical purposes, comprising a rod having a swab on at least one end thereof, with the rod being a continuous hollow extrusion including an outer shell provided with a continuous internal web.

2. Cotton ear swab device or swab used for medical purposes according to claim 1, wherein the internal web is connected once or several times to an internal surface of the shell, either continuously or in sections, with the webs being made of the same material as the shell.

3. A cotton ear swab or swab device used for medical purposes according to claim 2, wherein the internal web is connected to the internal surface of the shell at least at three points distributed about the circumference of the internal surface.

4. A cotton ear swab device or swab device used for medication purposes according to claim 3, wherein the internal web includes three webs extending radially from a center point and each connected to the internal surface of the shell at a respective point.

* * * * *

UNITED STATES PATENT AND TRADEMARK OFFICE
CERTIFICATE OF CORRECTION

PATENT NO. : 6,641,551 B1 Page 1 of 1
DATED : November 4, 2003
INVENTOR(S) : Robert Prager It is certified that error appears in the above-identified patent and that said Letters Patent is hereby corrected as shown below:

<u>Title page,</u>
Item [30], Foreign Application Priority Data, delete "199 18 426" and insert -- 199 18 242.6 --.

Signed and Sealed this

Sixteenth Day of March, 2004

JON W. DUDAS
*Acting Director of the United States Patent and Trademark Office*